(12) United States Patent
Jackson

(10) Patent No.: US 7,572,279 B2
(45) Date of Patent: *Aug. 11, 2009

(54) POLYAXIAL BONE SCREW WITH DISCONTINUOUS HELICALLY WOUND CAPTURE CONNECTION

(76) Inventor: Roger P. Jackson, 4706 W. 86th St., Prairie Village, KS (US) 66207

( * ) Notice: Subject to any disclaimer, the term of this patent is extended or adjusted under 35 U.S.C. 154(b) by 753 days.

This patent is subject to a terminal disclaimer.

(21) Appl. No.: 10/985,992

(22) Filed: Nov. 10, 2004

(65) Prior Publication Data

US 2006/0100621 A1   May 11, 2006

(51) Int. Cl.
*A61B 17/70* (2006.01)
(52) U.S. Cl. .................... 606/266; 606/269; 606/270
(58) Field of Classification Search ......... 606/264–275, 606/278–279, 300–320
See application file for complete search history.

(56) References Cited

U.S. PATENT DOCUMENTS

| | | | |
|---|---|---|---|
| 5,261,912 A | 11/1993 | Frigg | |
| 5,312,404 A | 5/1994 | Asher et al. | |
| 5,360,431 A | 11/1994 | Puno et al. | |
| 5,429,639 A | 7/1995 | Judet | |
| 5,443,467 A | 8/1995 | Biedermann et al. | |
| 5,466,237 A | 11/1995 | Byrd, III et al. | |
| 5,474,555 A | 12/1995 | Puno et al. | |
| 5,476,464 A | 12/1995 | Metz-Stavenhagen et al. | |
| 5,584,834 A | 12/1996 | Errico et al. | |
| 5,586,984 A | 12/1996 | Errico et al. | |
| 5,591,166 A | 1/1997 | Bernhardt et al. | |
| 5,601,553 A | 2/1997 | Trebing et al. | |

(Continued)

FOREIGN PATENT DOCUMENTS

DE   G9202745.8   4/1992

(Continued)

OTHER PUBLICATIONS

*EBI Omega 21* Brochure, EBI Spine Systems, pub. 1999.

(Continued)

*Primary Examiner*—Eduardo C Robert
*Assistant Examiner*—Mary Hoffman
(74) *Attorney, Agent, or Firm*—John C. McMahon

(57) ABSTRACT

A polyaxial bone screw assembly includes a threaded shank body having an upper capture structure, a head and an open, compressible retainer collar. The capture structure and retainer collar are both threaded for rotatable attachment within a cavity of the head. The head has a U-shaped cradle defining a channel for receiving a spinal fixation rod. The head channel communicates with the cavity and further with a restrictive opening that allows for loading the capture structure into the head but prevents passage of the attached retainer collar out of the head. The open retainer collar may be bottom- or top-loaded by compressing open ends of the ring towards each other, the collar springing back into a rounded shape after insertion in the head. The open collar has an external substantially spherical surface that mates with an internal surface of the head, providing a ball joint, enabling the head to be disposed at an angle relative to the shank body. The threaded capture structure includes a tool engagement formation and gripping surfaces for non-slip engagement by a tool for driving the shank body into bone.

45 Claims, 5 Drawing Sheets

U.S. PATENT DOCUMENTS

| | | |
|---|---|---|
| 5,669,911 A | 9/1997 | Errico et al. |
| 5,672,176 A | 9/1997 | Biedermann et al. |
| 5,690,630 A | 11/1997 | Errico et al. |
| 5,725,528 A | 3/1998 | Errico et al. |
| 5,728,098 A | 3/1998 | Sherman et al. |
| 5,733,286 A | 3/1998 | Errico et al. |
| 5,752,957 A | 5/1998 | Ralph et al. |
| 5,782,833 A | 7/1998 | Haider |
| 5,797,911 A | 8/1998 | Sherman et al. |
| 5,800,435 A | 9/1998 | Errico et al. |
| 5,817,094 A | 10/1998 | Errico et al. |
| 5,879,350 A | 3/1999 | Sherman et al. |
| 5,882,350 A | 3/1999 | Ralph et al. |
| 5,885,286 A | 3/1999 | Sherman et al. |
| 5,891,145 A | 4/1999 | Morrison et al. |
| 5,964,760 A | 10/1999 | Richelsoph |
| 6,010,503 A | 1/2000 | Richelsoph et al. |
| 6,019,759 A | 2/2000 | Rogozinski |
| 6,053,917 A | 4/2000 | Sherman et al. |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,090,110 A | 7/2000 | Metz-Stavenhagen |
| 6,090,111 A | 7/2000 | Nichols |
| 6,132,432 A | 10/2000 | Richelsoph |
| 6,146,383 A | 11/2000 | Studer et al. |
| 6,187,005 B1 | 2/2001 | Brace et al. |
| RE37,161 E | 5/2001 | Michelson et al. |
| 6,224,596 B1 | 5/2001 | Jackson |
| 6,248,105 B1 | 6/2001 | Schlapfer et al. |
| 6,254,602 B1 | 7/2001 | Justis |
| 6,273,888 B1 | 8/2001 | Justis |
| 6,280,442 B1 | 8/2001 | Barker et al. |
| 6,287,308 B1 | 9/2001 | Betz et al. |
| 6,287,311 B1 | 9/2001 | Sherman et al. |
| 6,302,888 B1 | 10/2001 | Mellinger et al. |
| 6,368,321 B1 | 4/2002 | Jackson |
| 6,471,705 B1 | 10/2002 | Biedermann et al. |
| 6,485,494 B1 | 11/2002 | Haider |
| 6,488,681 B2 | 12/2002 | Martin et al. |
| 6,554,834 B1 | 4/2003 | Crozet et al. |
| 6,565,565 B1 | 5/2003 | Yuan et al. |
| 6,565,567 B1 | 5/2003 | Haider |
| 6,623,485 B2 | 9/2003 | Doubler et al. |
| 6,695,843 B2 | 2/2004 | Biedermann et al. |
| 6,716,214 B1 | 4/2004 | Jackson |
| 7,066,062 B2 * | 6/2006 | Flesher ........................ 81/442 |
| 2001/0001119 A1 | 5/2001 | Lombardo |
| 2002/0111628 A1 * | 8/2002 | Ralph et al. .................... 606/61 |
| 2002/0143341 A1 | 10/2002 | Biedermann et al. |
| 2004/0106925 A1 * | 6/2004 | Culbert ........................ 606/73 |
| 2005/0055026 A1 * | 3/2005 | Biedermann et al. .......... 606/73 |
| 2005/0216000 A1 * | 9/2005 | Colleran et al. ............... 606/61 |
| 2005/0260058 A1 * | 11/2005 | Cassagne, III ............. 411/402 |
| 2006/0058788 A1 * | 3/2006 | Hammer et al. ............... 606/61 |

FOREIGN PATENT DOCUMENTS

| | | |
|---|---|---|
| DE | 19507141 | 9/1996 |
| EP | 1121902 | 8/2001 |

OTHER PUBLICATIONS

*Claris Instrumentation* Brochure, G Med, pub. 1997.
*VLS System Variable Locking Screw* Brochure, Interpore Cross International, 1999.
*CD Horizon M8 Multi Axial Screw Spinal System* Brochure, Medtronic Sofamor Danek, no publish date.
*Contour Spinal System* Brochure, Ortho Development, no publish date.
*Xia Spinal System* Brochure, Stryker Howmedica Osteonics, no publish date.
*The Rod Plate System* Brochure, Stryker Howmedica Osteonics, pub. Oct., 1999.
*Silhouette Spinal Fixation System* Brochure, Sulzer Medica Spine-Tech, no publish date.
*SDRS Surgical Dynamics Rod System* Brochure, Surgical Dynamics, pub. 1998-99.
*Versalok Low Back Fixation System* Brochure, Wright Medical Technology, Inc., pub. 1997.
*The Strength of Innovation* Advertisement, Blackstone Medical Inc., no publish date.
*The Moss Miami 6.0mm System* Advertisement, author unknown, no publish date.

\* cited by examiner

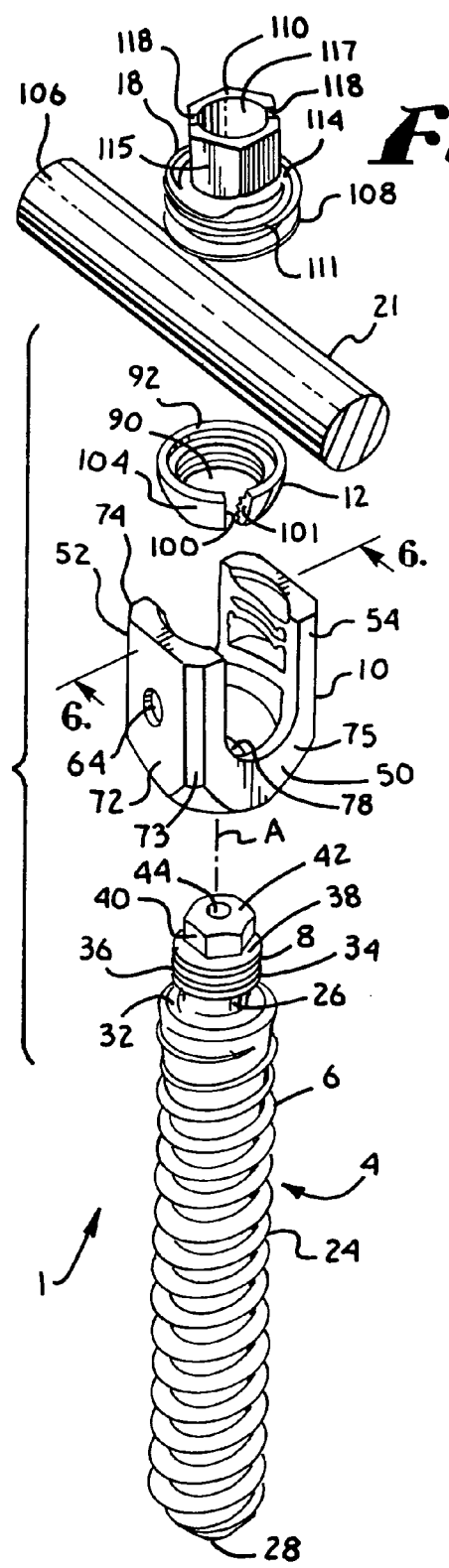
Fig. 1.
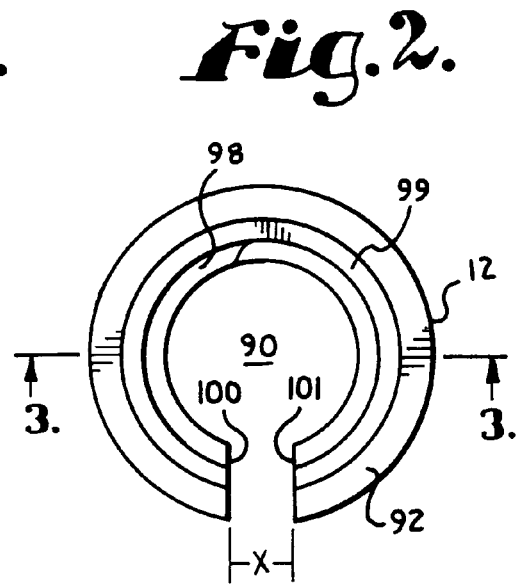
Fig. 2.
Fig. 3.
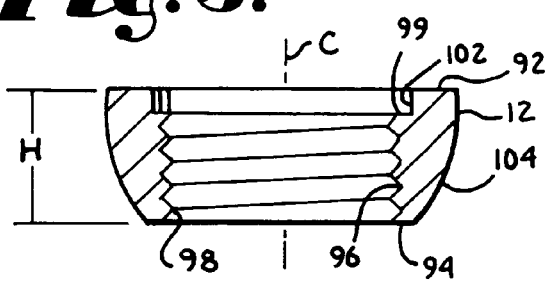
Fig. 4.
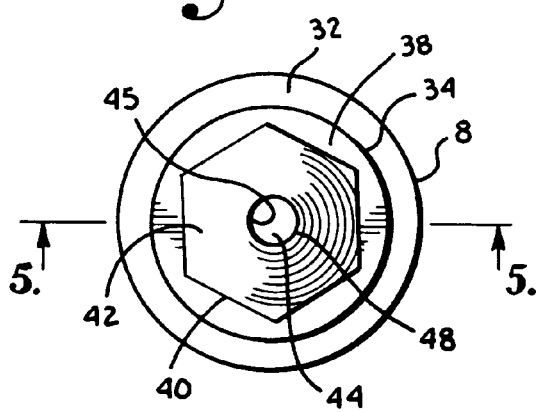

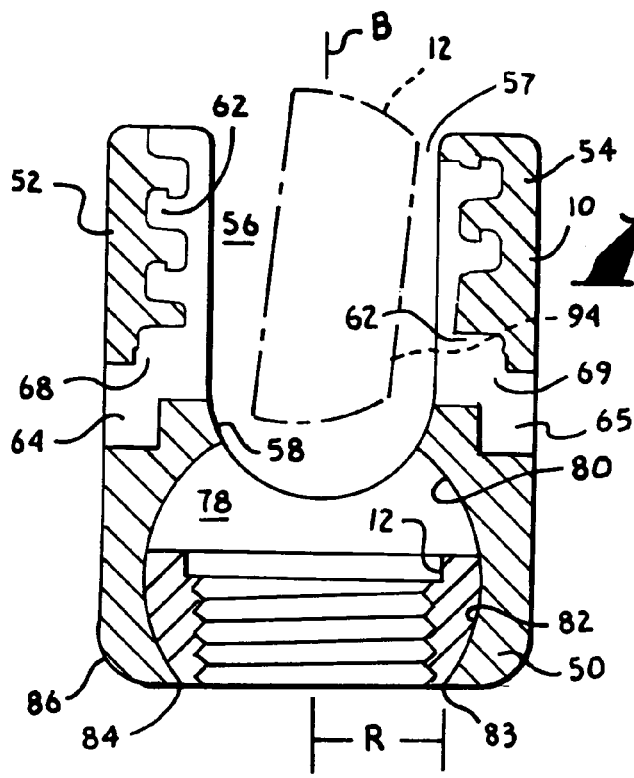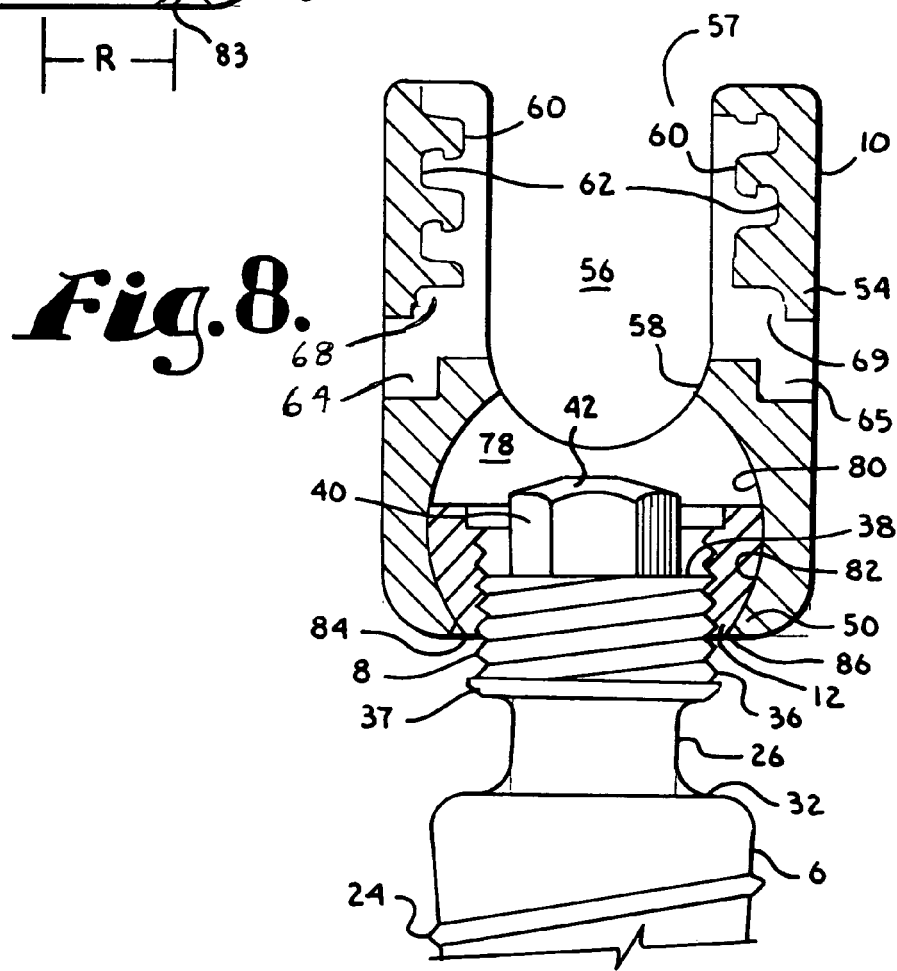

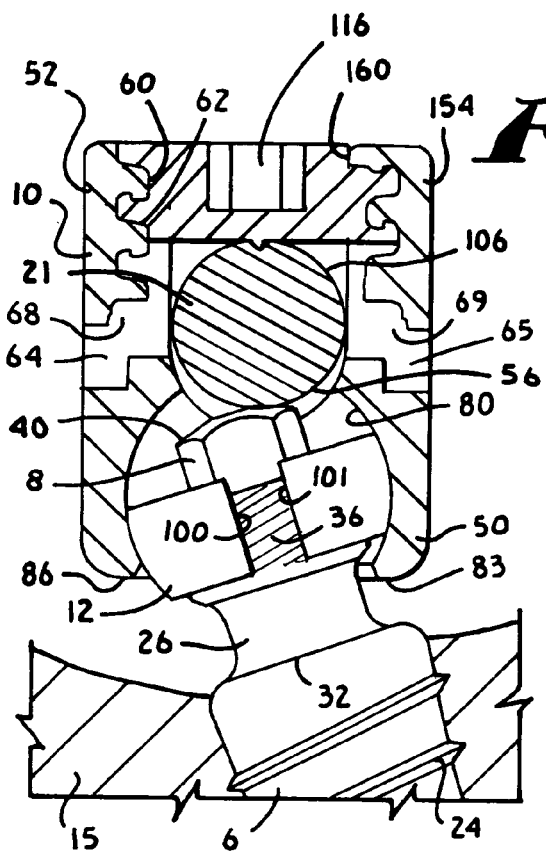
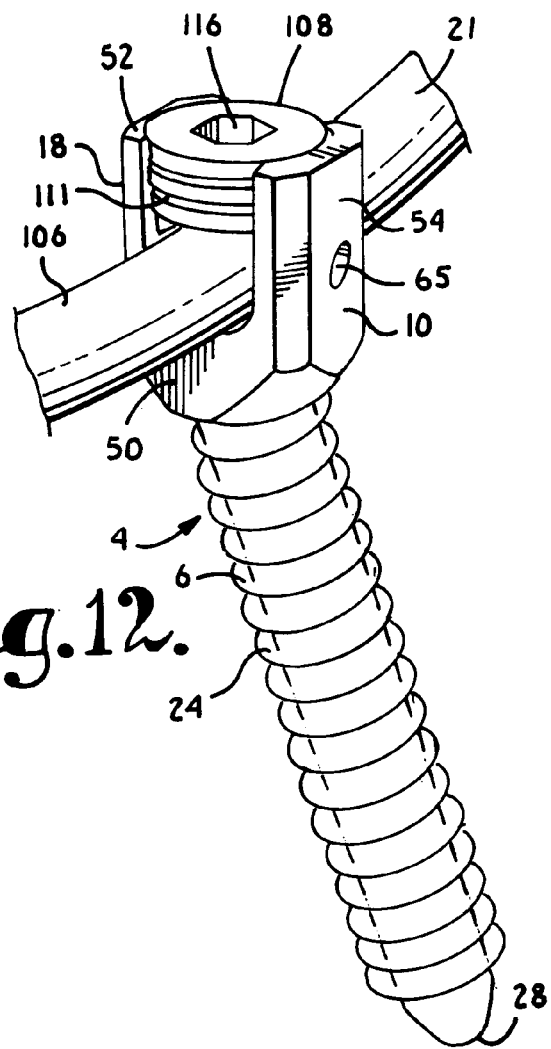

POLYAXIAL BONE SCREW WITH DISCONTINUOUS HELICALLY WOUND CAPTURE CONNECTION

BACKGROUND OF THE INVENTION

The present invention is directed to polyaxial bone screws for use in bone surgery, particularly spinal surgery. Such screws have a head that can swivel about a shank of the bone screw, allowing the head to be positioned in any of a number of angular configurations relative to the shank.

Many spinal surgery procedures require securing various implants to bone and especially to vertebrae along the spine. For example, elongate rods are often utilized that extend along the spine to provide support to vertebrae that have been damaged or weakened due to injury or disease. Such rods must be supported by certain vertebrae and support other vertebrae.

The most common mechanism for providing vertebral support is to implant bone screws into certain bones which then in turn support the rod or are supported by the rod. Bone screws of this type may have a fixed head relative to a shank thereof. In the fixed bone screws, the head cannot be moved relative to the shank and the rod must be favorably positioned in order for it to be placed within the head. This is sometimes very difficult or impossible to do. Therefore, polyaxial bone screws are commonly preferred.

Polyaxial bone screws allow rotation of the head about the shank until a desired rotational position of the head is achieved relative to the shank. Thereafter, a rod can be inserted into the head and eventually the head is locked or fixed in a particular position relative to the shank.

A variety of polyaxial or swivel-head bone screw assemblies are available. One type of bone screw assembly includes an open head that allows for placement of a rod within the head. A closure top or plug is then used to capture the rod in the head of the screw.

Because such implants are for placement within the human body, it is desirable for the implant to have as little effect on the body as possible. Consequently, heavy, bulky implants are undesirable and lighter implants with a relatively small profile both in height and width are more desirable. However, a drawback to smaller, lighter implants is that they may be more difficult to rigidly fix to each other and into a desired position. Lack of bulk may also mean lack of strength, resulting in slippage under high loading. Also, more component parts may be required to rigidly fix the implant in a desired position. A further drawback of smaller components is that they may be difficult to handle during surgery because of their small size, failing to provide adequate driving or gripping surfaces for tools used to drive the shank into bone or drive the closure top into the screw head.

One undesirable attribute of some of the swivel-head implants is the need for a multitude of components that may loosen or even disassemble within the body. It is most undesirable for components to be free to move around in the body after the completion of surgery. Loosening of components relative to each other may result in related undesirable movement of the bone or vertebra that the implant was intended to stabilize.

SUMMARY OF THE INVENTION

It is an object of the invention to overcome one or more of the problems described above. Further objects of the invention include: providing a polyaxial bone screw with features that provide adequate frictional or gripping surfaces for bone implantation tools and may be readily, securely fastened to each other and to bone. Also, if the implant should slip or become loose for some reason, an object of the invention is to provide an implant wherein all of the parts remain together and do not separate. Furthermore, it is an object of the invention to provide a lightweight, low profile polyaxial bone screw that assembles in such a manner that the components cooperate to create an overall structure that prevents unintentional disassembly.

A polyaxial bone screw assembly of the present invention includes a shank having a body for fixation to a bone. Integral with the shank and extending axially upwardly and outwardly therefrom is a capture structure. The capture structure has a radially projecting outer surface that is substantially cylindrical and that further includes a helically wound structure, such as a thread. The upper end of the shank is convexly curved.

The bone screw assembly further includes a head having a top portion and a base. The top portion is open and has a channel. The base also is upwardly open and includes an inner seating surface partially defining a cavity and has a lower aperture or opening. The channel of the top portion communicates with the cavity, which in turn communicates with an exterior of the base of the head through the base opening. The base opening is sized and shaped to receive the capture structure of the shank into the head cavity.

The bone screw assembly also includes an open collar or ring-like retainer structure that has an internal surface with a discontinuous helically wound structure thereon, such as a thread. The thread of the retainer structure is sized and shaped to mate with the thread of the shank capture structure when the retainer structure and the capture structure are coaxially aligned within the head cavity, thereby securing the retainer structure to the capture structure. In an embodiment according to the invention, a distance between ends of the open collar-like retainer structure is sufficient to allow for pinching of the ends toward one another and resulting compression of the ring to be receivable or up-loadable into the base opening of the head. A lesser distance between retainer structure ends results in a down-loadable embodiment receivable into the head channel. The retainer structure springs back into a rounded shape once disposed in the head cavity. When loaded for locking, pressure from structure above causes the retainer structure to expand radially within the head cavity, thereby improving the frictional fixation between the retainer structure and the head inner seating surface.

The external surface of the retainer structure is configured to be in slidable mating engagement with the surface defining the cavity of the head. Preferably, the retainer structure external surface and the mating head inner surface are substantially similar and spherical. However, it is noted that the mating surfaces may be of another shape, such as conical or tapered, especially for the inner surface of the head cavity. The cooperating shapes of the retainer external surface and the head inner surface enable selective angular positioning of the shank body with respect to the head.

In one embodiment according to the invention, the capture structure includes a tool engagement formation that extends or projects from the capture structure and is located between the curved upper end and the threaded cylindrical portion thereof. The tool formation is for non-slip engagement by a tool for driving the shank into bone and may also be cooperatively used for attaching the retainer structure to the capture structure.

Also according to the invention are tool seating surfaces that may be disposed on one or both of the capture structure and the retainer structure. In one embodiment, the shank capture structure includes tool engagement surfaces that are positioned and shaped to receive a socket type tool and a planar, tool seating surface extending radially from the lower end of the tool engagement surfaces. The seating surface is disposed coaxially with the shank body. The open retainer structure has mating seating surfaces that cooperate with the shank capture structure seating surface. The tool seating surfaces and the tool engagement surfaces partially define a recess for receiving a driving tool mating with the tool engagement surfaces. When engaged, the driving tool is in contact with the capture structure tool seating surface, providing greater mating surface to the capture structure tool engagement surfaces so as to provide additional surface for frictional gripping when the shank body is driven into bone.

In certain embodiments a tool seating and partially surrounding surface may be disposed on the retainer structure according to the invention such that when the retainer structure is mated with the capture structure, the retainer structure seating surface extends radially from the lower end of the tool engagement surfaces and is disposed coaxially with respect to the shank body.

In certain embodiments, both the capture structure and the retainer structure may include tool seating surfaces that extend radially in the same plane when the capture structure and the retainer structure are mated. In such embodiments, the two tool seating surfaces and the shank tool engagement surfaces partially define a recess for receiving a driving tool engaged with the tool engagement surfaces. When engaged, the driving tool is in contact with both tool seating surfaces, thereby seating the tool lower relative to the tool engagement surfaces and providing additional frictional gripping surface when the shank body is driven into bone.

A polyaxial bone screw assembly method according to the invention includes uploading or downloading an open collar-like retainer structure into a head cavity by compressing the structure during insertion, inserting a capture structure of a bone screw shank through a shank receiving opening of the head and into a cavity thereof; and attaching the capture structure to the retainer structure within the head cavity.

A method according to the invention further includes driving the shank body into bone by rotating the shank body with a tool engaged with a tool engagement formation, such as a pair of aligned and spaced slots, disposed on the capture structure or the retainer structure. Further assembly steps according to the invention include inserting a rod into the channel; and biasing the rod against a top of the bone screw shank capture structure by rotatably inserting a closure member structure within or onto a mating structure of the rod receiving channel structure.

It is to be understood that while certain forms of the present invention have been illustrated and described herein, it is not to be limited to the specific forms or arrangement of parts described and shown.

Other objects and advantages of this invention will be apparent to those skilled in the art from the following description taken in conjunction with the drawings and the appended claims.

The drawings constitute a part of this specification and include exemplary embodiments of the present invention and illustrate various objects and features thereof.

BRIEF DESCRIPTION OF THE DRAWINGS

FIG. 1 is an exploded perspective view of a polyaxial bone screw assembly according to the present invention having a shank with a capture structure at one end thereof, a head, and an open collar-like retainer structure and further showing a rod and closure structure.

FIG. 2 is an enlarged top plan view of the open retainer structure of FIG. 1.

FIG. 3 is an enlarged cross-sectional view of the open retainer structure of FIG. 2, taken along line 3-3 of FIG. 2.

FIG. 4 is an enlarged top plan view of the shank of FIG. 1.

FIG. 7 is an enlarged cross-sectional view of the head according to FIG. 6, and showing the retainer structure seated in the head (in solid lines) and illustrating the retainer structure being downloaded into the head (in dashed lines).

FIG. 8 is an enlarged cross-sectional view of the head and retainer structure similar to FIG. 7, showing the shank capture structure partially threaded into the retainer structure.

FIG. 11 is an enlarged, fragmentary cross-sectional view of the head, rod and vertebra, similar to FIG. 9 and further showing the closure member structure in contact with the rod and the rod in contact with the capture structure.

FIG. 12 is a fragmentary and enlarged perspective view of the assembly of FIG. 1 shown completely assembled.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 9:
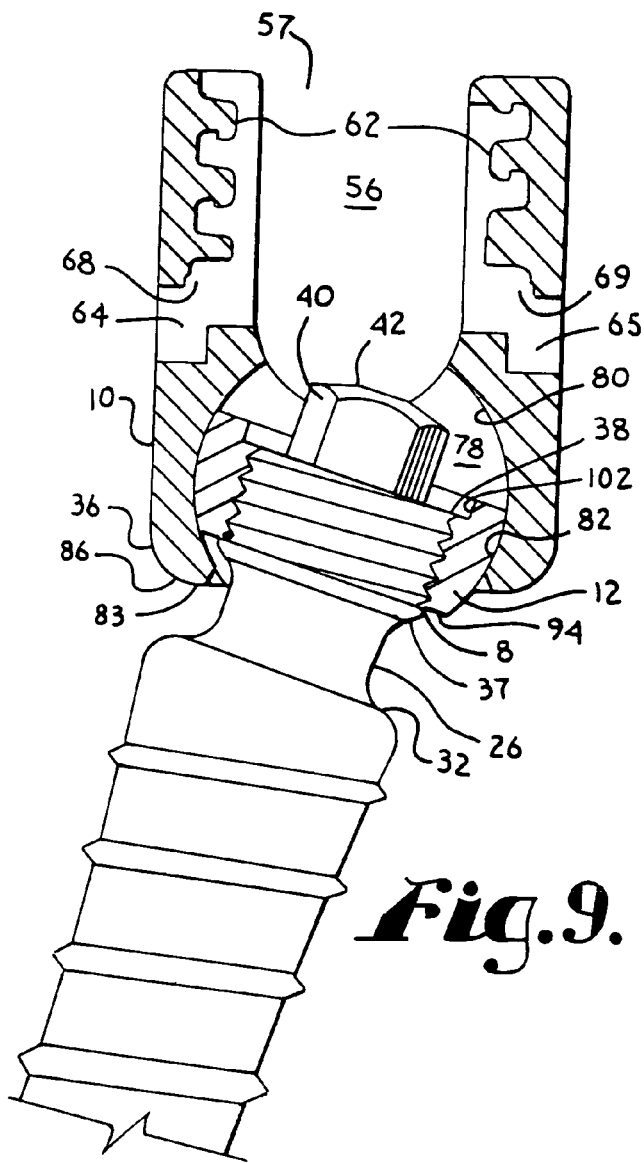
FIG. 9 is an enlarged cross-sectional view of the head and retainer structure similar to FIG. 8, illustrating the fully assembled shank and retainer structure pivoted to a selected angle relative to the head.
Figure 10:
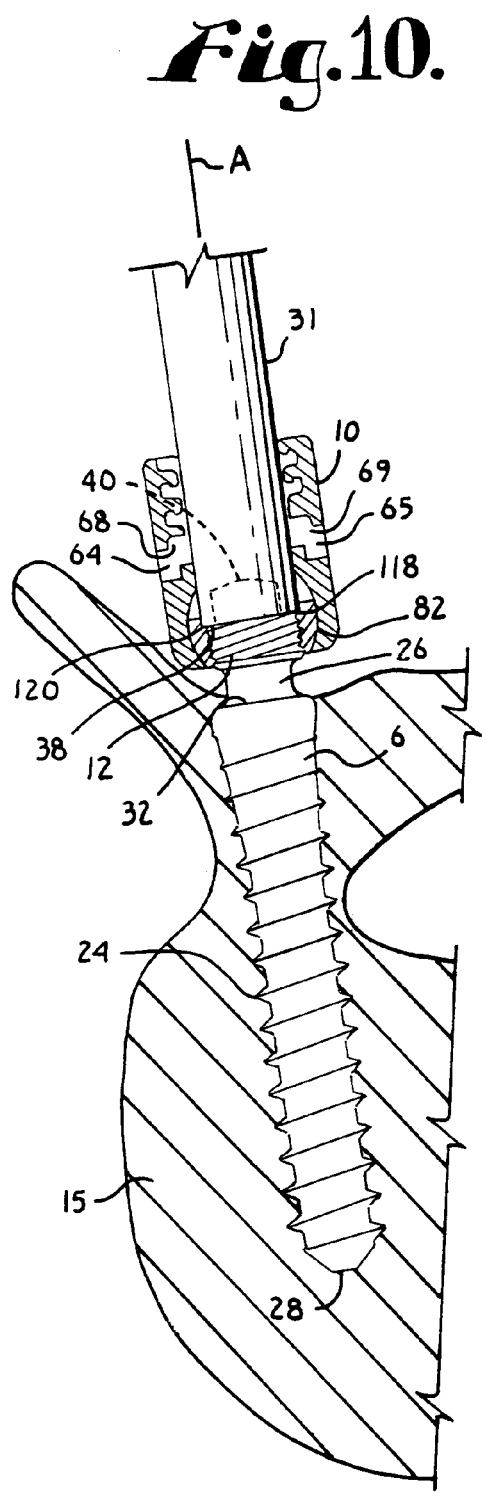
FIG. 10 is an enlarged cross-sectional view of a vertebra, and head and retainer similar to FIG. 9, showing the shank being implanted into the vertebra using a driving tool mounted on the shank capture structure.

In FIGS. 1-12 the reference number 1 generally represents a first embodiment of a polyaxial bone screw apparatus or assembly according to the present invention. The assembly 1 includes a shank 4 that further includes a body 6 integral with an upwardly extending capture structure 8; a head 10; and an open retainer structure or discontinuous ring or collar 12. The shank 4, head 10 and open retainer structure 12 preferably are assembled prior to implantation of the shank body 6 into a vertebra 15, which procedure is shown in FIG. 10.

FIG. 1 further shows a closure structure 18 of the invention for compressing and biasing a longitudinal member such as a rod 21 against the capture structure 8 which biases the open collar 12 into fixed frictional contact with the head 10, so as to fix the rod 21 relative to the vertebra 15. The head 10 and shank 4 cooperate in such a manner that the head 10 and shank 4 can be secured at any of a plurality of angles, articulations or rotational alignments relative to one another and within a selected range of angles both from side to side and from front to rear, to enable flexible or articulated engagement of the head 10 with the shank 4 until both are locked or fixed relative to each other near the end of an implantation procedure.

Figure 5:
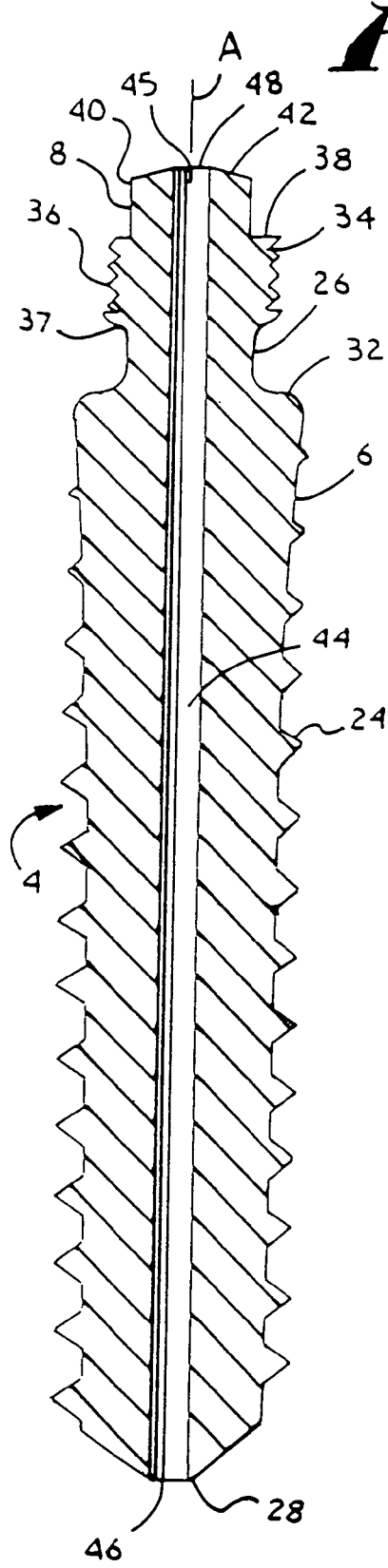
FIG. 5 is an enlarged cross-sectional view of the shank, taken along line 5-5 of FIG. 4.

The shank 4, best illustrated in FIGS. 1 and 5, is elongate, with the shank body 6 having a helically wound bone implantable thread 24 extending from near a neck 26 located adjacent to the capture structure 8 to a tip 28 of the body 6 and extending radially outward therefrom. During use, the body 6 utilizing the thread 24 for gripping and advancement is implanted into the vertebra 15 leading with the tip 28 and driven down into the vertebra 15 with an installation or driving tool 31, so as to be implanted in the vertebra 15 to near the neck 26, as shown in FIG. 9, and as is described more fully in the paragraphs below. The shank 4 has an elongate axis of rotation generally identified by the reference letter A. It is noted that any reference to the words top, bottom, up and down, and the like, in this application refers to the alignment shown in the various drawings, as well as the normal connotations applied to such devices, and is not intended to restrict positioning of the assembly 1 in actual use.

The neck 26 extends axially outward and upward from the shank body 6. The neck 26 is of reduced radius as compared to an adjacent top 32 of the body 6. Further extending axially and outwardly from the neck 26 is the capture structure 8 that provides a connective or capture apparatus disposed at a distance from the body top 32 and thus at a distance from the vertebra 15 when the body 6 is implanted in the vertebra 15.

The capture structure 8 is configured for connecting the shank 4 to the head 10 and capturing the shank 4 in the head 10. The capture structure 8 has an outer substantially cylindrical surface 34 having a helically wound advancement structure thereon which in the illustrated embodiment is a V-shaped thread 36 disposed adjacent to a seating surface 38 and extending to a location near a rim 37. The rim 37 is adjacent to the neck 26. Although a simple thread 36 is shown in the drawings, it is foreseen that other structures including other types of threads, such as buttress and reverse angle threads, and non threads, such as helically wound flanges with interlocking surfaces, may be alternatively used in alternative embodiments of the present invention. The cylindrical surface 34 could be truncated giving a non-contiguous helically wound structure.

The shank 4 further includes a tool engagement structure 40 disposed near a top end surface 42 thereof for engagement of the driving tool 31 shown in FIG. 9 which includes a driving structure in the form of a socket. The tool 31 is configured to fit about the tool engagement structure 40 so as to form a socket and mating projection for both driving and rotating the shank body 6 into the vertebra 15. Specifically in the embodiment shown in FIGS. 1-12, the tool engagement structure 40 is in the shape of a hexagonally shaped extension head coaxial with both the threaded shank body 6 and the threaded capture structure 8.

The top end surface 42 of the shank 4 is preferably curved or dome-shaped as shown in the drawings, for simple smooth contact engagement or positive mating engagement with the rod 21, when the bone screw assembly 1 is assembled, as shown in FIGS. 11 and 12 and in any alignment of the shank 4 relative to the head 10. In certain embodiments, the surface 42 is smooth. While not required in accordance with practice of the invention, the surface 42 may be scored, knurled or the like to further increase frictional positive mating engagement between the surface 42 and the rod 21.

The shank 4 shown in the drawings is cannulated, having a small central bore 44 extending an entire length of the shank 4 along the axis A. The bore 44 is defined by an inner cylindrical wall 45 of the shank 4 and has a first circular opening 46 at the shank tip 28 and a second circular opening 48 at the top surface 42. The bore 44 is coaxial with the threaded body 6 and the capture structure outer surface 34. The bore 44 provides a passage through the shank 4 interior for a length of wire (not shown) inserted into the vertebra 15 prior to the insertion of the shank body 6, the wire providing a guide for insertion of the shank body 6 into the vertebra 15.

Referring to FIGS. 1 and 6 through 10, the head 10 has a generally U-shaped appearance with a partially cylindrical inner profile and a faceted outer profile. The head 10 includes a somewhat spherical base 50 integral with a pair of upstanding arms 52 and 54 forming a U-shaped cradle and defining a U-shaped channel 56 between the arms 52 and 54 with an upper opening 57 and a lower seat 58 having substantially the same radius as the rod 21 for operably snugly receiving the rod 21.

Each of the arms 52 and 54 has an interior surface 60 that defines the inner cylindrical profile and includes a partial helically wound guide and advancement structure 62. In the illustrated embodiment, the guide and advancement structure 62 is a partial helically wound interlocking flange form configured to mate under rotation with a similar structure on the closure top 18, as described more fully below. However, it is foreseen that the guide and advancement structure 62 could alternatively be a V-shaped thread, a buttress thread, a reverse angle thread or other thread like or non-thread like helically wound advancement structures for operably guiding under rotation and advancing the closure top downward between the arms 52 and 54.

Tool engaging apertures 64 and 65 are formed within the arms 52 and 54, respectively which may be used for holding the head 10 during assembly with the shank 4 and the open retainer structure 12 and also during the implantation of the shank body 6 into a vertebra 15.

Communicating with the apertures 64 and 65 are respective upwardly projecting, hidden inner recesses 68 and 69. The holding tool (not shown) is sized and shaped to have structure to mate with and to be received in the apertures 64 and 65 and locked into place by pulling the holding tool slightly axially upward relative to the base 50 and toward the upper opening 57 of the channel 56 formed by the arms 52 and 54. The holding tool and respective apertures 64 and 65 can be configured for a flexible snap on/spring off engagement wherein the holding tool has flexible legs which splay outwardly to position the tool for engagement in the apertures 64 and 65. It is noted that the apertures 64 and 65 and the cooperating holding tool may be configured to be of a variety of sizes and locations along any of the surfaces of the arms 52 and 55, for example, extending into a face 75 or disposed only at a single face or facet.

Communicating with and located beneath the U-shaped channel 56 of the head 10 is a chamber or cavity 78 substantially defined by an inner surface 80 of the base 50, the cavity 78 opens upwardly into the U-shaped channel 56. The inner surface 80 is substantially spherical, with at least a portion thereof forming a partial internal spherical seating surface 82 having a first radius. The surface 82 is sized and shaped for mating with the open retainer structure 12, as described more fully below.

The base 50 further includes a restrictive neck 83, having a second radius R and defining a bore 84 communicating with the cavity 78 and a lower exterior 86 of the base 50. The bore 84 is coaxially aligned with respect to a rotational axis B of the head 10. The neck 83 and associated bore 84 are sized and shaped to be smaller (the second radius) than a radial dimension of the open, uncompressed retainer structure 12 (the first radius), as will be discussed further below, so as to form a restriction at the location of the neck 83 relative to the retainer structure 12, to prevent the uncompressed retainer structure 12 from passing from the cavity 78 and out into the lower exterior 86 of the head 10 when the retainer structure 12 is seated and loaded.

The open retainer structure or collar 12 is used to retain the capture structure 8 of the shank 4 within the head 10. The open retainer structure 12, best illustrated by FIGS. 1-3, 6-9 and 11, has an operational central axis that is the same as the elongate axis A associated with the shank 4, but when the open retainer structure 12 is separated from the shank 4, the axis of rotation is identified as axis C, as shown in FIG. 3. The open retainer structure 12 has a central channel or bore 90 that passes entirely through the open retainer structure 12 from a top surface 92 to a bottom surface 94 thereof. A first inner, discontinuous cylindrical surface 96 defines a substantial portion of the bore 90, the surface 96 having a discontinuous helically wound advancement structure thereon as shown by a helical rib or thread 98 extending from adjacent the bottom surface 94 to adjacent a flat, discontinuous seating surface 99 disposed perpendicular to the inner surface 96.

Although a simple helical rib 98 is shown in the drawings, it is foreseen that other helical structures including other types of threads, such as buttress and reverse angle threads, and non threads, such as helically wound flanges with interlocking surfaces, may be alternatively used in an alternative embodiment of the present invention. The inner cylindrical surface 96 with helical rib 98 are configured to mate under rotation with the capture structure outer surface 34 and helical advancement structure or thread 36, as described more fully below.

Figure 6:
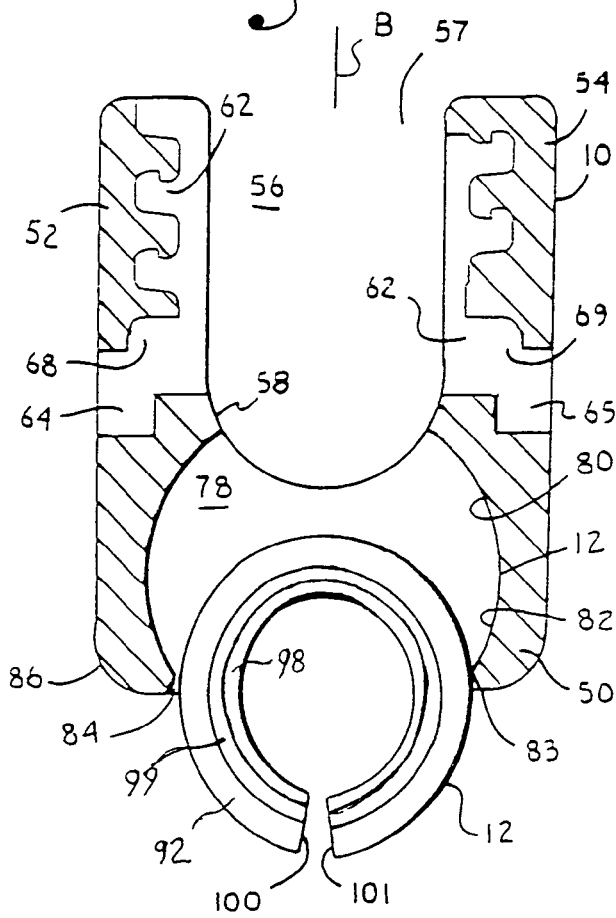
FIG. 6 is an enlarged cross-sectional view of the head, taken along the line 6-6 of FIG. 1 and a top plan view of the open retainer structure, similar to the view shown in FIG. 3, illustrating the open retaining structure being compressed during uploading into the head.

The open retainer structure 12 includes first and second end surfaces, 100 and 101 disposed in spaced relation to one another. Both end surfaces 100 and 101 are disposed substantially perpendicular to the top surface 92 and the bottom surface 94. A width X between the surfaces 100 and 101 is determined by a desired amount of compressibility of the open retainer structure 12 when loaded into the head 10. The space X shown in FIG. 2 provides adequate space between the surfaces 100 and 101 for the open retainer structure or collar 12 to be pinched, with the surfaces 100 and 101 compressed toward one another as shown in FIG. 6, to an extent that the compressed collar 12 is in a substantially oval shape and thus up-loadable into the head cavity 78 through the bore 84 defined by the restrictive neck 83. After passing through the bore 84, the open retainer structure 12 expands or springs back to an uncompressed, rounded or collar-like configuration of FIGS. 2 and 3, once in the cavity 78.

If desired, in other embodiments according to the invention (not shown) the width X may be smaller than that shown in FIG. 2, with the collar ends 100 and 101 disposed at a closer relation than what is shown in FIG. 2. Such a collar may be compressed, or not, for down-loading through the channel 56 as shown in FIG. 7, but not through the bore 84.

The embodiment shown in FIG. 2 also illustrates the surfaces 100 and 101 as substantially parallel and vertical, however, it is foreseen that it may be desirable to orient the surfaces obliquely or at a slight angle depending upon the amount of compression desired during loading of the open retainer structure 12 into the head 10.

The open retainer structure 12 further includes a discontinuous second inner wall or substantially cylindrical surface 102, coaxial with the first discontinuous inner cylindrical surface 96. The surface 102 is disposed between the seating surface 99 and the top surface 92 of the open retainer structure 12 and has a diameter greater than that of the cylindrical surface 96. As will be described more fully below, the cylindrical surface 102 in cooperation with the seating surface 99 and the surface 38 of the open retainer structure 12, provide a recess about the base of the tool engagement structure 40 and a stable seating surface for the tool 31, as shown in FIG. 9. The wall 102 which is the outer wall of the recess may be shaped to fit an outer surface of the tool 31 and may be faceted or especially hexagonal in shape to better grip the tool 31.

The open retainer structure or collar 12 has a radially outer partially spherically shaped surface 104 sized and shaped to mate with the partial spherical shaped seating surface 82 of the head and having a third radius approximately equal to the first radius associated with the surface 82. The retainer structure third radius is larger than the second radius R of the neck 83 of the head 10. Although not required, it is foreseen that the outer partially spherically shaped surface 104 may be a high friction surface such as a knurled surface or the like.

The elongate rod or longitudinal member 21 that is utilized with the assembly 1 can be any of a variety of implants utilized in reconstructive spinal surgery, but is normally a cylindrical elongate structure having a cylindrical surface 106 of uniform diameter and having a generally smooth surface. The rod 21 is preferably sized and shaped to snugly seat near the bottom of the U-shaped channel 56 of the head 10 and, during normal operation, is positioned slightly above the bottom of the channel 56 at the lower seat 58. In particular, the rod 21 normally directly or abuttingly engages the shank top surface 42, as shown in FIG. 10 and is biased against the dome shank top surface 42, consequently biasing the shank 4 downwardly in a direction toward the base 50 of the head 10 when the assembly 1 is fully assembled. For this to occur, the shank top surface 42 must extend at least slightly into the space of the channel 56 when the open retainer structure 12 is snugly seated in the lower part of the head cavity 80. The shank 4 and the open retainer structure 12 are thereby locked or held in position relative to the head 10 by the rod 21 firmly pushing downward on the shank top surface 42.

With reference to FIGS. 1, 11 and 12, the closure structure or closure top 18 can be any of a variety of different types of closure structures for use in conjunction with the present invention with suitable mating structure on the upstanding arms 52 and 54. In the embodiment shown, the closure top 18 is rotatably received between the spaced arms 52 and 54. It is foreseen that a mating and advancement structure could be located on the external surfaces of the arms 52 and 54 for mating with a closure top.

The illustrated closure top 18 has a generally cylindrical shaped base 108 with an upwardly extending break-off head 110. The base 108 includes a helically wound guide and advancement structure 111 that is sized, shaped and positioned so as to engage the guide and advancement structure 62 on the arms 52 and 54 to provide for rotating advancement of the closure structure 18 into the head 10 when rotated clockwise and, in particular, to cover the top or upwardly open portion of the U-shaped channel 56 to capture the rod 21, preferably without splaying of the arms 52 and 54. The closure structure 18 also operably biases against the rod 21 by advancement and applies pressure to the rod 21 under torquing, so that the rod 21 is urged downwardly against the shank top end surface 42 that extends into the channel 56. Downward biasing of the shank top surface 42 operably produces a frictional engagement between the rod 21 and surface 42 and also urges the open retainer structure 12 toward the base 50 of the head 10, so as to frictionally seat the retainer structure external spherical surface 104 fixedly against the partial internal spherical seating surface 82 of the head 10, also fixing the shank 4 and the open retainer structure 12 in a selected, rigid position relative to the head 10. At this time it is also possible for the retainer to expand somewhat for an even tighter fit in the head cavity.

The closure structure break-off head 110 is secured to the base 108 at a neck 114 that is sized and shaped so as to break away at a preselected torque that is designed to properly seat the open retainer structure 12 in the head 10. The break-off head 110 includes an external faceted surface 115 that is sized and shaped to receive a conventional mating socket type head of a driving tool (not shown) to rotate and torque the closure structure 18. The break-off head 110 also includes a central bore 117 and grooves 118 for operably receiving manipulating tools.

The closure structure 18 also includes removal tool engagement structure which in the present embodiment is in the form of a hex-shaped and axially aligned aperture 116 disposed in the base 108, as shown in FIGS. 11 and 12. The hex aperture 116 is accessible after the break-off head 110 breaks away from the base 108. The aperture 116 is coaxial with the helically wound guide and advancement structure 111 and is designed to receive a hex tool, of an Allen wrench type, into the aperture 116 for rotating the closure structure base 108 subsequent to installation so as to provide for removal thereof, if necessary. Although a hex-shaped aperture 116 is shown in the drawings, the tool engagement structure may take a variety of tool-engaging forms and may include one or more apertures of various shapes, such as a pair of spaced apart apertures, or a left hand threaded bore, or an easyout engageable step down bore, or a Torx aperture, or a multi-lobular aperture or the like.

Prior to the polyaxial bone screw assembly 1 being placed in use according to the invention, the open collar-like retainer structure 12 is first inserted or bottom-loaded into the head cavity 78 as shown in FIG. 6, by first manually compressing the structure 12 by pinching the surfaces 100 and 101 toward one another and then inserting the compressed structure 12 into the bore 84 that opens to the lower exterior surface 86 of the head 10. After the retainer structure 12 moves beyond the bore 84 and into the cavity 78, the compressive force is removed and the open retainer structure 12 resiliently returns to a former ring-like or collar-like orientation. Alternatively, the open retainer structure 12 may be top-loaded into the head U-shaped channel 56, as is shown in dotted lines in FIG. 7, utilizing some compression if necessary, and then placed into the cavity 78 to dispose the structure 12 within the inner surface 80 of the head 10. Then, the open retainer structure 12 is rotated or otherwise manipulated so as to be coaxial with the head 10 and then seated in sliding engagement with the seating surface 82 of the head 10, also shown in FIG. 7. In this way and at this time the retainer can have a stable spring-loaded fit within the head cavity.

With reference to FIG. 8, the shank capture structure 8 is then inserted or bottom-loaded into the head 10 through the bore 84 defined by the neck 83. The open retainer structure 12, now disposed in the head 10 is coaxially aligned with the shank capture structure 8 so that the helical advancement structure 36 rotatingly mates with the discontinuous helical advancement structure 98 of the open retainer structure 12.

The shank 4 and or the open retainer structure 12 are rotated to fully mate the structures 36 and 98 along the respective cylindrical surfaces 34 and 96, as shown in FIG. 8, fixing the capture structure 8 to the open retainer structure 12, until the seating surface 38 and the seating surface 99 are contiguous and disposed in the same plane and the rim 37 abuts the surface 94 of the open retainer structure 12 as shown in FIG. 9. Permanent, rigid engagement of the capture structure 8 to the open retainer structure 12 may be further ensured and supported by the use of adhesive, a spot weld, deforming one or both threads with a punch or the like.

As shown in FIG. 9, at this time the shank 4 is in slidable and rotatable engagement with the head 10, while the capture structure 8 and the lower aperture or neck 83 of the head 10 cooperate to maintain the shank body 6 in rotational relation with the head 10. According to the embodiment of the invention shown in FIGS. 1-12, only the open retainer structure 12 is in slidable engagement with the head spherical seating surface 82. Both the capture structure 8 and threaded portion of the shank body 6 are in spaced relation with the head 10.

It is believed that an advantage to this embodiment is that, although the shank 6 could engage the head lower aperture or neck 83 when rotated fully relative to the head 10 as best illustrated in FIG. 9, upper shank body 6 does not contact the lower spherical seating surface 82, so that rotational stresses between the capture structure 8 and the open retainer structure 12 are lessened, making it less likely that the open retainer structure 12 would loosen from the capture structure 8 or that the capture structure would fail or break when the assembly 1 is implanted and loaded.

An extent of rotation is shown in FIG. 9 where it is illustrated that the shank body 6 can be rotated through a substantial angular rotation relative to the head 10, both from side to side and from front to rear so as to substantially provide a universal or ball joint wherein the angle of rotation is only restricted by engagement of the neck 26 of the shank body 6 with the neck or lower aperture 83 of the head 10.

With reference to FIG. 10, the assembly 1 is then typically screwed into a bone, such as the vertebra 15, by rotation of the shank 4 using the driving tool 31 that operably drives and rotates the shank 4 by engagement thereof with the hexagonally shaped extension head 40 of the shank 4. Preferably, when the driving tool 31 engages the head 40, an end portion 118 thereof is disposed in a recess defined by the head 40, the seating surface 38, the contiguous seating surface 99 and the inner cylindrical surface 102, with a bottom surface 119 of the tool 31 contacting and frictionally engaging both the seating surface 38 and the seating surface 99. Some frictional engagement between an outer surface 120 of the tool 31 with the cylindrical surface 102 may also be achievable during rotation of the driving tool 31.

It is foreseen that in other embodiments according to the invention, the tool engaging recess may be defined by only one of the seating surface 38 or the seating surface 99. For example, a retainer structure might not include a seating surface, so a driving tool might seat or mate only with a seating surface or an internal aperture of a shank capture structure. Alternatively, the tool engaging end of a capture structure might be of a size and shape that a driving tool substantially seats on a seating surface of a retainer structure or ring and not the capture structure.

Typically, the head 10 and the open retainer structure 12 are assembled on the shank 4 before inserting the shank body 6 into the vertebra 15, but in certain circumstances, the shank body 6 can be first partially implanted with the capture structure 8 extending proud to allow assembly with the head 10 utilizing the open retainer structure 12. Then the shank body 6 can be further driven into the vertebra 15.

With reference to FIGS. 1 and 5 as well as FIG. 10, the vertebra 15 may be pre-drilled to minimize stressing the bone and have a guide wire (not shown) that is shaped for the cannula 44 inserted to provide a guide for the placement and angle of the shank 4 with respect to the vertebra 15. A further tap hole may be made using a tap with the guide wire as a guide. Then, the assembly 1 or the solitary shank 4, is threaded onto the guide wire utilizing the cannulation bore 44 by first threading the wire into the bottom opening 46 and then out of the top opening 48. The shank 4 is then driven into the vertebra 15, using the wire as a placement guide.

With reference to FIGS. 1, 11 and 12, the rod 21 is eventually positioned within the head U-shaped channel 56, and the closure structure or top 18 is then inserted into and advanced between the arms 52 and 54 so as to bias or push against the rod 21. The break-off head 110 of the closure structure 18 is twisted to a preselected torque, for example 90 to 120 inch pounds, to urge the rod 21 downwardly. The shank top end surface 42, because it is rounded to approximately equally extend upward into the channel 56 approximately the same amount no matter what degree of rotation exists between the shank 4 and head 10 and because the surface 42 is sized to extend upwardly into the U-shaped channel 56, the surface 42 is engaged by the rod 21 and pushed downwardly toward the base 50 of the head 10 when the closure structure 18 biases downwardly toward and onto the rod 21. The downward pressure on the shank 4 in turn urges the open retainer structure 12 downward toward the head seating surface 82, with the retainer structure seating surface 99 in further frictional engagement with the head seating surface 82. As the closure structure 18 presses against the rod 21, the rod 21 presses against the shank and the open retainer structure 12 that is now rigidly attached to the shank 4 which in turn becomes frictionally and rigidly attached to the head 10, fixing the shank body 6 in a desired angular configuration with respect to the head 10 and rod 21. The applied compression through the mating threads further urges the open retainer structure to spread thereby increasing the frictional fixation.

FIG. 10 illustrates the polyaxial bone screw assembly 1 and including the rod 21 and the closure structure 18 positioned in a vertebra 15. The axis A of the bone shank 4 is illustrated as not being coaxial with the axis B of the head 10 and the shank 4 is fixed in this angular locked configuration. Other angular configurations can be achieved, as required during installation surgery due to positioning of the rod 21 or the like.

If removal of the assembly 1 and associated rod 21 and closure structure 18 is necessary, disassembly is accomplished by using a driving tool of an Allen wrench type (not shown) mating with the aperture 116 and turned counterclockwise to rotate the base 108 and reverse the advancement thereof in the head 10. Then, disassembly of the assembly 1 is accomplished in reverse order to the procedure described previously herein for assembly.

It is to be understood that while certain forms of the present invention have been illustrated and described herein, it is not to be limited to the specific forms or arrangement of parts described and shown.

What is claimed and desired to be secured by Letters Patent is as follows:

1. A polyaxial bone screw assembly comprising:
   (a) a shank having a body for fixation to a bone and a capture structure extending from the body, the capture structure having an outer surface with a first helically wound guide and advancement structure;
   (b) a head having a top portion and a base, the head top portion defining an open channel, the base having a seating surface partially defining a cavity, the channel communicating with the cavity, the cavity communicating with an exterior of the base through an opening sized and shaped to receive the capture structure therethrough; and
   (c) an open discontinuous retainer structure having an external surface and a central channel with an internal surface having a discontinuous second helically wound guide and advancement structure thereon, the first helically wound guide and advancement structure configured to rotatably mate with the second helically wound guide and advancement structure to secure the retainer structure to the capture structure within the head cavity, the external surface configured to be in slidable mating engagement with the seating surface of the head so as to enable selective angular positioning of the shank body with respect to the head, the shank and retainer structure mating in the head so as to allow polyaxial rotation thereof relative to the head and with the shank extending above the retainer structure, the shank having an external tool engagement formation thereon to engage a driving tool with the tool engagement structure being accessible to the tool when the shank and retainer structure are mated.

2. The assembly of claim 1 wherein:
   (a) the head seating surface that is located to be in slidable mating engagement with the retainer structure external surface is substantially spherical; and
   (b) the open retainer structure external surface that is in slidable mating engagement with the head seating surface is substantially spherical.

3. The assembly of claim 1 wherein the capture structure tool engagement formation is an axial projection having a hexagonal profile.

4. The assembly of claim 1 wherein the tool engagement formation is a projection and the open retainer structure has a tool seating surface, the projection and the tool seating surface partially defining a recess for receiving a driving tool engaged with the tool engagement projection and wherein the driving tool is adapted to be in contact with the tool seating surface when driving the shank body into bone.

5. The assembly of claim 1 wherein the tool engagement formation is a projection and the capture structure has a tool seating surface, the projection and the tool seating surface partially defining a recess about a base of the projection adapted for receiving a driving tool engaged with the tool engagement projection and wherein the driving tool is adapted to be in contact with the tool seating surface when driving the shank body into bone.

6. The assembly of claim 1 wherein the tool engagement formation is a projection, the open retainer structure has a first seating surface, and the capture structure has a second seating surface; the projection, the first seating surface and the second seating surface partially defining a recess at a base of the projection adapted for receiving a driving tool engaged with the tool engagement projection and wherein the driving tool is adapted to be in contact with both the first and second seating surfaces when driving the shank body into bone.

7. The assembly of claim 1 wherein the open retainer structure further comprises first and second spaced ends.

8. The assembly of claim 7 wherein the open retainer structure is compressible and expandable, the first and second ends being movable toward and away from one another.

9. The assembly of claim 1 wherein the open retainer structure is sized and shaped to be at least one of downloadable and up-loadable into the head.

10. The assembly of claim 1 wherein the first helically wound guide and advancement structure is a raised helical rib.

11. The assembly of claim 1 wherein the second helically wound guide and advancement structure is a raised helical rib.

12. The assembly of claim 1 wherein the shank is cannulated.

13. The assembly of claim 1 wherein the open retainer structure has a first planar seating surface and the capture structure has a second planar seating surface, the first and second planar seating surfaces being in contact when the retainer structure is secured to the capture structure.

14. The assembly of claim 13 wherein the open retainer structure has a second internal surface, the second internal surface and the first planar seating surface partially defining a recess, the second planar seating surface disposed in the recess when the retainer structure is secured to the capture structure.

15. The assembly of claim 1 wherein the open retainer structure is sized and shaped to be loadable into the head through the open channel and the shank is sized and shape to be loadable into the head through the base opening.

16. The assembly of claim 1 further comprising a closure structure insertable into the head, the closure structure for operably urging the shank in a direction to frictionally lock the position of the retainer structure external surface relative to the head seating surface, thereby locking the shank body in a selected angle with respect to the head.

17. The assembly of claim 16 wherein:
  (a) the head has upstanding spaced arms defining the open channel, the arms having guide and advancement structures on an inside surface thereof; and
  (b) the closure structure is sized and shaped to be positionable between the arms for closing the channel, the closure structure having a closure guide and advancement structure for rotatably mating with the guide and advancement structures on the arms, biasing the closure structure upon advancement rotation against a rod disposed in the channel.

18. The assembly of claim 16 wherein the capture structure end has a dome sized and shaped to extend into the channel for engagement with a rod when received in the head and wherein the closure structure is adapted to operably urge the rod against the dome upon the closure structure being positioned in the head.

19. In a polyaxial bone screw assembly for surgical implantation and including a shank having an upper end and a threaded body for inserting into a bone and a head having an outward opening channel adapted to receive a rod within the channel, the head having a shank receiving opening, the improvement comprising:
  (a) a capture structure disposed on the shank upper end sized and configured to be uploaded through the shank receiving opening, the capture structure having an outer surface with a first helically wound advancement structure; and
  (b) an open retainer structure having an external surface and an internal surface with a discontinuous second helically wound advancement structure, the first helically wound advancement structure configured to rotatably mate with the second helically wound advancement structure to secure the open retainer structure to the capture structure within the head, when assembled and in a non locked configuration, the open retainer structure external surface enabling selective angular positioning of the shank with respect to the head, the shank capture structure extending above the retainer structure when fully assembled and having a tool engagement formation thereon that is accessible by a driving tool when the capture structure and retainer structure are fully assembled.

20. The improvement of claim 19 wherein:
  (a) the head has an inner substantially spherical seating surface partially defining a cavity, the cavity communicating with both the channel and the shank receiving opening; and
  (b) the open retainer structure external surface is substantially spherical and in slidable mating engagement with the head seating surface.

21. The improvement of claim 19 wherein the tool engagement formation is radially disposed thereon and sized and shaped for non-slip engagement by a tool for driving the shank body into bone.

22. The improvement of claim 21 wherein the tool engagement formation is a projection and the open retainer structure has a tool seating surface, the projection and the tool seating surface partially defining a recess for receiving a driving tool engaged with the tool engagement projection and wherein the driving tool is adapted to be in contact with the tool seating surface when driving the shank body into bone.

23. The improvement of claim 21 wherein the tool engagement formation is a projection and the capture structure has a tool seating surface, the projection and the tool seating surface partially defining a recess about a base of the projection adapted for receiving a driving tool engaged with the tool engagement projection and wherein the driving tool is adapted to be in contact with the tool seating surface when driving the shank body into bone.

24. The improvement of claim 21 wherein the tool engagement formation is a projection, the open retainer structure has a first seating surface, and the capture structure has a second seating surface; the projection, the first seating surface and the second seating surface partially defining a recess adapted for receiving a driving tool engaged with the tool engagement projection and wherein the driving tool is adapted to be in contact with both the first and second seating surfaces when driving the shank body into bone.

25. The improvement of claim 19 wherein the open retainer structure has first and second ends in spaced relation, the retainer structure being compressible.

26. The improvement of claim 25 wherein the open retainer structure is both up-loadable and down-loadable into the head.

27. The improvement of claim 19 wherein the first helically wound advancement structure is a raised helical rib.

28. The improvement of claim 27 wherein the second helically wound advancement structure is a raised helical rib.

29. The improvement of claim 19 wherein the open retainer structure has a first planar seating surface and the capture structure has a second planar seating surface, the first and second planar seating surfaces being in contact when the retainer structure is secured to the capture structure.

30. A polyaxial bone screw assembly comprising:
  (a) a shank having a threaded body for fixation to a bone and a capture structure extending from the body, the capture structure having an outer substantially cylindrical surface with a first raised helical rib disposed thereon;
  (b) a head having a top portion and a base, the top portion defining an open channel, the base having a partial substantially spherical seating surface partially defining a cavity, the channel communicating with the cavity, the cavity communicating with an exterior of the base through an opening therein sized and shaped to receive the capture structure therethrough;
  (c) an open, compressible, retainer structure having first and second ends, an external partial spherical surface and an internal substantially cylindrical surface having a discontinuous second raised helical rib disposed thereon, the first rib configured to rotatably mate with the second rib to secure the retainer structure to the capture structure within the head cavity with the external surface oriented in slidable mating engagement with the seating surface of the head when in a non locked configuration; and
  (d) a tool engagement formation disposed on the capture structure and extending above the retainer structure when the retainer structure is fully mated with the shank capture structure within the head, the formation adopted for non-slip engagement by a tool for driving the shank body into bone.

31. The assembly of claim 30 wherein the tool engagement formation is a projection extending axially from the capture structure and the open retainer structure has a tool seating surface, the projection and the tool seating surface partially defining a recess about a base of the projection adapted for receiving a driving tool engaged with the tool engagement projection and wherein the driving tool is adapted to be in contact with the tool seating surface when driving the shank body into bone.

32. The assembly of claim 30 wherein the tool engagement formation is a projection extending axially from the capture structure and the capture structure has a tool seating surface, the projection and the tool seating surface partially defining a recess about a base of the projection adapted for receiving a driving tool engaged with the tool engagement projection and wherein the driving tool is adapted to be in contact with the tool seating surface when driving the shank body into bone.

33. The assembly of claim 30 wherein the tool engagement formation is a projection extending axially from the capture structure, the retainer structure has a first seating surface, and the capture structure has a second seating surface; the projection, the first seating surface and the second seating surface defining a recess adapted for receiving a driving tool engaged with the tool engagement projection and wherein the driving tool is adapted to be in contact with both the first and second seating surfaces when driving the shank body into bone.

34. The assembly of claim 30 wherein the open retainer structure has a first planar seating surface and the capture structure has a second planar seating surface, the first and second planar seating surfaces being in contact when the retainer structure is secured to the capture structure.

35. The assembly of claim 34 wherein the retainer structure has a second internal surface, the second internal surface and the first planar seating surface partially defining a recess, the second planar seating surface being disposed in the recess when the retainer structure is secured to the capture structure.

36. The assembly of claim 30 wherein the retainer structure is sized and shaped to be both down-loadable into the head through the open channel and up-loadable through the base opening, and the shank is sized and shape to be loadable into the head through the base opening.

37. The assembly of claim 30 further comprising a closure structure insertable into the head, the closure structure closing a top of the channel and adapted to operably urge the shank in a direction to frictionally fix the retainer external surface to the head seating surface, thereby rigidly positioning the shank body in a selected angle with respect to the head.

38. The assembly of claim 37 wherein:
(a) the head has upstanding spaced arms defining the open channel, each of the arms having guide and advancement structures on an inside surface thereof; and
(b) the closure structure is disposable between the arms for closing the channel, the closure structure having an advancement structure for rotatably mating with the guide and advancement structures on the arms, thereby biasing the closure structure against a rod disposed in the channel when rotated in an advancement direction.

39. The assembly of claim 38 wherein the capture structure end has a dome sized and shaped to be adapted for engagement with a rod when received in the head and wherein the closure structure is adapted to operably urge the rod against the dome upon the closure structure being positioned in the head.

40. In a polyaxial bone screw assembly for surgical implantation and including a shank having a capture end and an elongate threaded body having an axis of rotation for being driven by rotation into a bone, and a head having an outward opening channel adapted to receive a rod within the channel, the head further having an inner cavity and a shank receiving opening, the improvement comprising:
(a) a capture structure disposed on the shank capture end sized and configured to be receivable through the shank receiving opening, the capture structure having a tool engagement projection extending therefrom; and
(b) an open retainer structure configured to mate with the capture structure within the head cavity so as to polyaxially rotate with the capture structure relative to the head cavity with the capture structure extending above the retainer structures when mated, and the capture structure having a planar tool seating surface that is on the exterior of the shank and that is accessible by the tool when the retainer structure is mated with the capture structure and that extends along the projection and is disposed coaxial with the shank body when the retainer structure is mated with the capture structure.

41. The improvement of claim 40 wherein the at least one tool seating surface is disposed on the capture structure, the projection and the capture structure tool seating surface partially defining a recess adapted for receiving a driving tool engaged with the projection and wherein the driving tool is adapted to be in contact with the capture structure tool seating surface when driving the shank body into bone.

42. The improvement of claim 40 wherein the at least one tool seating surface is disposed on the open retainer structure, the projection and the retainer structure tool seating surface partially defining a recess adapted for receiving a driving tool engaged with the projection and wherein the driving tool is adapted to be in contact with the retainer structure tool seating surface when driving the shank body into bone.

43. The improvement of claim 40 wherein the at least one tool seating surface is a first tool seating surface on the capture structure and a second tool seating surface on the open retainer structure, the projection and the first and second tool seating surfaces partially defining a recess adapted for receiving a driving tool engaged with the projection and wherein the driving tool is adapted to be in contact with both the first and second tool seating surfaces when driving the shank body into bone.

44. The improvement of claim 40 wherein:
(a) the capture structure has an outer cylindrical surface with a first raised helically wound rib thereon; and
(b) the open retainer structure has a discontinuous external surface and a discontinuous inner cylindrical surface with a second raised helically wound rib thereon, the first helically wound rib configured to rotatably mate with the second helically wound rib to secure the retainer structure to the capture structure within the head cavity, and the retainer structure external surface enabling selective angular positioning of the shank with respect to the head.

45. The improvement of claim 44 wherein:
(a) the head has an inner substantially spherical seating surface partially defining the cavity; and
(b) the open retainer structure discontinuous external surface is substantially spherical and in slidable mating engagement with the head seating surface.

* * * * *